United States Patent [19]

Carlin et al.

[11] Patent Number: 4,845,104
[45] Date of Patent: Jul. 4, 1989

[54] OXIDIZED ANALOGS OF 17β-N-MONOSUBSTITUTED-CARBAMOYL-4-AZA-5-α-ANDROSTAN-3-ONES

[75] Inventors: Josephine R. Carlin, North Brunswick; Gary H. Rasmusson, Watchung; W. J. A. VandenHeuvel, Princeton, all of N.J.

[73] Assignee: Merck & Co., Inc., Rahway, N.J.

[21] Appl. No.: 932,550

[22] Filed: Nov. 20, 1986

[51] Int. Cl.[4] .................. C07J 73/00; A61K 31/58
[52] U.S. Cl. ...................... 514/284; 546/77
[58] Field of Search .......... 514/176, 284; 546/77

[56] References Cited

U.S. PATENT DOCUMENTS

| | | | |
|---|---|---|---|
| 4,104,285 | 8/1978 | Gallo-Torres | 260/397.1 |
| 4,191,759 | 3/1980 | Johnston et al. | 540/110 |
| 4,220,775 | 9/1980 | Rassmusson | 546/77 |
| 4,732,897 | 3/1988 | Cainelli | 546/77 |
| 4,760,071 | 7/1988 | Rasmusson | 514/284 |

OTHER PUBLICATIONS

Rassmusson II, J. Med. Chem 29, 2298-2315.

Primary Examiner—Mark L. Berch
Attorney, Agent, or Firm—Charles M. Caruso; Hesna J. Pfeiffer

[57] ABSTRACT

The compounds of formula (I)

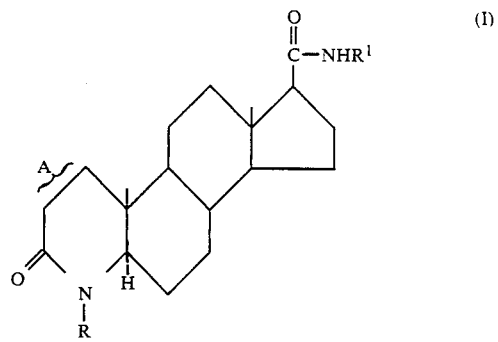

wherein R is selected from hydrogen, methyl or ethyl, and $R^1$ is $C_{1-12}$ straight or branched chain alkyl wherein one of the hydrogens is substituted by hydroxy, carboxylic acid or $C_{1-4}$ alkyl ester, and A is $-CH_2-CH_2$ or $-CH=CH-$, and pharmaceutical formulations of the above compounds are active as testosterone 5α-reductase inhibitors and thus are useful for treatment of acne, seborrhea, female hirsutism or benign prostatic hypertrophy.

9 Claims, No Drawings

OXIDIZED ANALOGS OF 17β-N-MONOSUBSTITUTED-CARBAMOYL-4-AZA-5-α-ANDROSTAN-3-ONES

BACKGROUND OF THE INVENTION

The present invention is concerned with novel oxidized analogs of 17β-N-monosubstituted carbamoyl-4-aza-5α-androstan-3-one compounds and the use of such compounds as testosterone-5α-reductase inhibitors.

It is well known in the art that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4′-nitro-3′-trifluoromethylisobutyranilide. See Neri et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfeh et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotesterone caused enlargement of the female hamster flank organ, an androgen dependent sebaceous structure. However, concommitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steroid compounds are known. See, for example, U.S. Pat. Nos. 2,227,876; 3,239,417; 3,264,301; and 3,285,918; French Pat. No. 1,465,544; Doorenbos and Solomons, J. Pharm. Sci. 62, 4, pp. 638–640 (1973); Doorenbos and Brown, J. Pharm. Sci., 60 8, pp. 1234–1235 (1971); and Doorenbos and Kim, J. Pharm. Sci. 63, 4, pp. 620–622 (1974).

In addition U.S. Pat. No. 4,377,584 and 4,220,775 and EP Appln. No. 4949 of Rasmusson et al. describe a group of 4-aza-17β-substituted-5α-androstan-3-ones which are useful in the treatment of hyperandrogenic conditions. Recently, a number of investigators from Merck & Co., Inc. have published regarding the biological activity of 5α-reductase inhibitors. See for example, Rasmusson et al., J. Med. Chem. 29: 2298–2315 (1986), Brooks et al., The Prostate 9: 65–75 (1986), Liang et al., Endocrinology 117, No. 2, pp. 571–579 (1985), Rasmusson et al., J. Med. Chem. 27: 1690–1701 (1984), Liang et al., J. Biol. Chem. 259, No. 2, pp. 734–739 (1984). The biological activity of 17β-(N-t-butylcarbamoyl)-4-aza-androst-1-en-3-one has also been reported. However, only the Rasmusson et al. (1986) reference teaches or suggests that any of the novel oxidized analogs of 17βN-(monosubstituted)carbamoyl-4-aza-5α-androstan-3-ones of the present invention would have utility as highly potent testosterone-5α-reductase inhibitors.

In addition to being 5α-reductase inhibitors and thus useful for the treatment of benign prostatic hypertrophy, acne vulgaris, seborrhea and hirsutism, certain of the compounds of the present invention are metabolites resulting from in vivo administration of 17β-(N-t-butylcarbamoyl)-4-aza-5α-androst-1-en-3-one. In many cases, metabolism of active drug result in deactivation and/or excretion, however, in this case the compounds of the present invention maintain a sustained high level of bioactivity in treated animals and have prolonged half-lifes.

DESCRIPTION OF THE INVENTION

The present invention is concerned with novel oxidized analogs of 17β-N-(monosubstituted)-carbamoyl-4-aza-5α-androstan-3 one compounds, pharmaceutical formulations comprising the novel compounds as active ingredients and methods of inhibiting testosterone-5α-reductase and of treating hyperandrogenic conditions with the novel compounds or their pharmaceutical formulations.

The present invention is concerned with compounds of the formula:

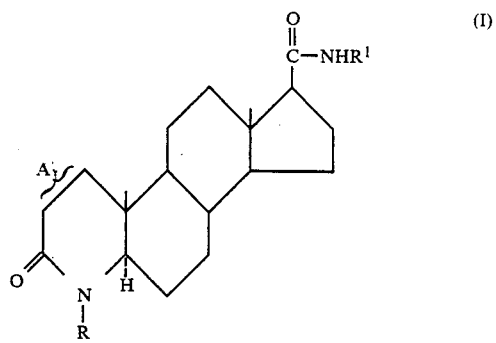

wherein
R is hydrogen, methyl or ethyl;
$R^1$ is $C_{1-12}$ straight or branched chain alkyl wherein one of the hydrogens is substituted by hydroxy, carboxylic acid or $C_{1-4}$ alkyl ester; and
A is —CH$_2$—CH$_2$— or —CH=CH—, or the pharmaceutically acceptable salts thereof.

A preferred embodiment of the novel compounds of our invention is represented by the formula:

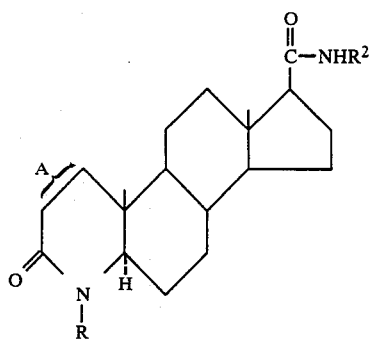

(II)

wherein

R is hydrogen, methyl or ethyl; and $R^2$ is $C_{3-8}$ branched chain alkyl wherein one of the hydrogens is substituted by hydroxy, carboxylic acid or $C_{1-4}$ alkyl ester; and A is —$CH_2$—$CH_2$— or —CH=CH—.

A more preferred embodiment is represented by the formula II compounds wherein R is hydrogen or methyl, $R^2$ is $C_{3-8}$ branched chain alkyl wherein one of the hydrogens is substituted by hydroxy, carboxylic acid or $C_{1-4}$ alkyl ester, and A is —C=C—.

Representative compounds of the present invention include the following:

17β-N-(2-hydroxymethyl-2-propyl)carbamoyl-4-aza-5α-androst-1-en-3-one;

17β-N-(2-hydroxymethyl-2-propyl)carbamoyl-4-aza-5α-androstan-3-one;

17β-N-(2-carboxy-2-propyl)carbamoyl-4-aza-5α-androst-1-en-3-one;

17β-N-(2-carboxy-2-propyl)carbamoyl-4-aza-5α-androstan-3-one;

17β-N-(2-carbomethoxy-2-propyl)carbamoyl-4-aza-5α-androst-1-en-3-one;

17β-N-(2-carbomethoxy-2-propyl)carbamoyl-4-aza-5α-androstan-3-one;

and the corresponding compounds wherein the 4-hydrogen substituent is replaced in each of the above named compounds by a methyl radical.

Also included as representative compounds are any of the above indicated compounds where the side chain alkyl substituent is replaced by a branched chain, such as i-propyl, i-butyl, s-butyl, t-butyl, i-pentyl, s-pentyl, t-pentyl, etc.

The novel compounds of formula I of the present invention are prepared by a method starting with the steroid ester of the formula shown in Rasmusson et al., J. Med. Chem., 29: 2298–2315 (1986) which is incorporated by reference:

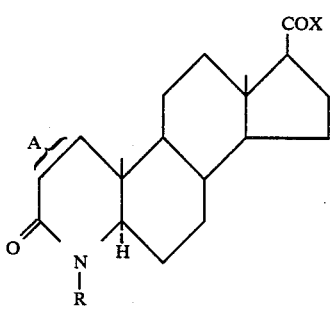

(III)

A is —$CH_2$—$CH_2$— or —CH=CH—,

R is H, $CH_3$, $C_2H_5$,

X is Cl,

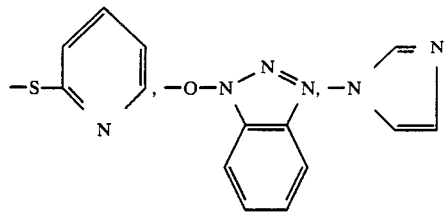

The above reactions are schematically represented in the following structural formula outline.

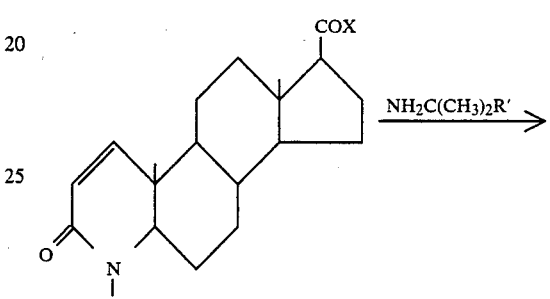

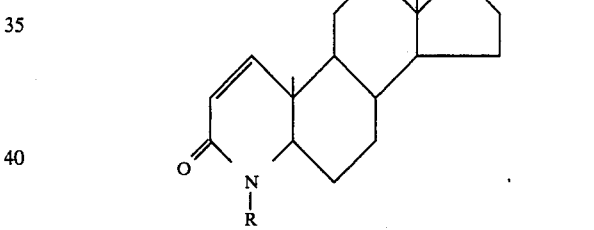

R' = $CH_2OH$, $CO_2CH_3$

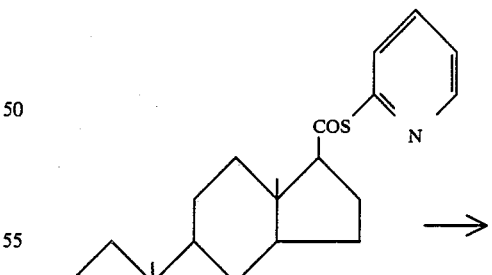

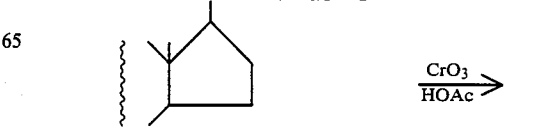

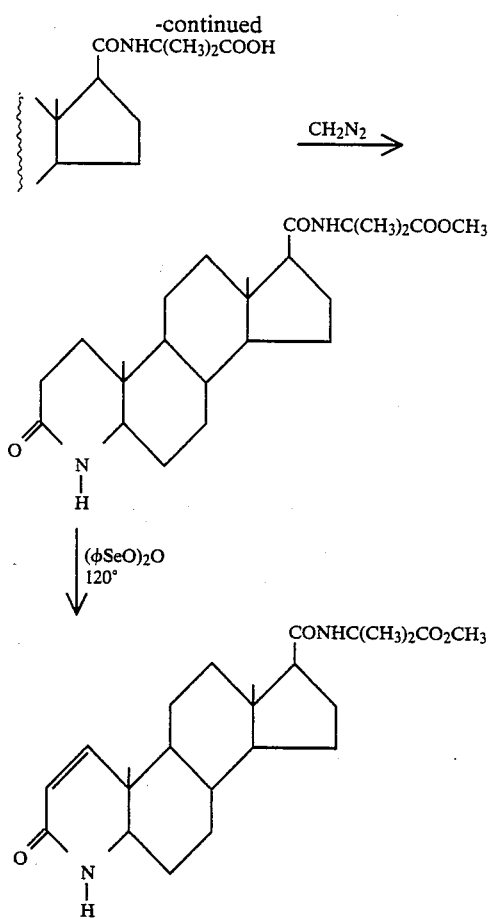

In general, a functionalized alkyl amine is reacted with a suitably reactive derivative of the 17β-carboxyazasteroid to form the corresponding 17β-carboxamide. The side-chain or nucleus of the steroid can be further modified by standard synthetic reactions.

The compounds of the present invention, prepared in accordance with the method described above, are, as already described, potent antiandrogens by virtue of their ability to specifically inhibit testosterone-5α-reductase.

Additionally, certain of the compounds of the present invention are metabolites resulting from in vivo administration of 17β-(N-t-butylcarbamoyl)-4-aza-androst-1-en-3-one. Thus, a major plasma metabolite is the side-chain hydroxylated (monohydroxymethyl) species of Example 1. An acidic metabolite resulting from further oxidation of the monohydroxymethyl species was identified as the compound of Example 2. An additional metabolite was identified as the compound of Example 3. Thus, these metabolic products in substantially pure form are also an aspect of the present invention.

Accordingly, the present invention is particularly concerned with providing a method of treating the hyperandrogenic conditions of acne vulgaris, seborrhea, and female hirsutism, as well as benign prostatic hypertrophy, by systemic or topical administration of the novel compounds of the present invention.

The present invention is also concerned with providing suitable topical and systemic pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 10 to 2,000 mg. The compositions are preferably provided in the form of tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 0.25 mg. to about 50 mg./kg. of body weight per day. Preferably the range is from about 1 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservative are employed when intravenous administration is desired.

For topical administration, the pharmaceutical composition comprises the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 2%, of the active compound, in admixture with about 8% of vehicle.

The method of preparing the novel compounds of the present invention, already described above in general terms, may be further illustrated by the following examples.

EXAMPLE 1

17β-N-(2-hydroxymethyl-2-propyl)carbamoyl-4-aza-5α-androst-1-en-3-one

A mixture of 100 mg of 3-oxo-4-aza-5α-androst-1-ene-17β-carboxylic acid, 69 mg of dicyclohexylcarbodiimide and 77 mg of N-hydroxybenztriazole in 5 ml of methylene chloride was stirred at 0° C. for 30 minutes and then at 24° C. for 16 hours. To the resulting solution of activated ester was added 150 μl of 2-amino-2-methylpropanol. After 5 hours the mixture was filtered and the solid was rinsed with methylene chloride. The combined filtrates were evaporated and the residue was chromatographed on a silica coated thin layer plates (4, 1000μ×20 cm ×20 cm) with 8% methanol in chloroform. The major component was extracted and isolated. Recrystallization from acetonitrile-methanol gave 41 mg of the product, m.p. 282°–287° C.

EXAMPLE 2

17β-N-(2-carboxy-2-propyl)carbamoyl-4-aza-5α-androst1-ene-3-one

To a solution of 53 mg of chromium trioxide in 1.2 ml of glacialacetic acid was added 85 mg of the product of Example 1. The resulting solution was heated at 35° C. for 12 hours and then cooled to room temperature. Water (30 ml) was added and the separated product was extracted with chloroform. The chloroform solution was washed with water and dried before concentration to the residue. Crystallization from ethyl acetate gives 40 mg of the product.

EXAMPLE 3

17β-N-(2-carbomethoxy-2-propyl)carbamoyl-4-aza-androst-1-en-3-one

To a solution of 22 mg of the product of Example 2 in 3.0 ml of tetrahydrofuran was added a slight excess of diazomethane as a solution in diethyl ether. After 10 minutes at room temperature sufficient glacial acetic acid was added to consume all the diazomethane. The solution was concentrated and the residue was crystallized from ethyl acetate to give 15 mg of the product.

Alternately, this product can be prepared by the following procedure: A solution of 20 mg of 17β-N-(2-carbomethoxy-2-propyl)carbamoyl-4-aza-5α-androstan-3-one (Example 9 below) and 50 mg of benzeneseleninic anhdyride in 0.8 ml of chlorobenzene is heated at reflux for 3 hours. After cooling ethyl acetate and water are added and the phases are separated. The organic layer is washed with dilute sodium bicarbonate solution and then dried and concentrated. The product is isolated by thin layer chromatography on silica eluted with chloroform-acetone (2:1) and is identified by its mass spectrum (molecular ion, 416).

EXAMPLE 4

17β-N-(2-hydroxymethyl-2-propyl)carbamoyl-4-methyl-4-aza-5α-androstan-3-one

A suspension of 0.5 g of 4-methyl-3-oxo-4-aza-5-androstane-17β-carboxylic acid was stirred in a solution of 1.2 ml of oxalyl chloride in 6.5 ml of toluene at room temperature for 20 minutes. The reaction was concentrated under reduced pressure to a residue which was redissolved in tetrahydrofuran. To this solution was added 1.0 ml of 2-methyl-2-aminopropanol. After 1 hour at room temperature ice water was added and the mixture was extracted with methylene chloride. The organic solution was washed successively with 2N hydrochloric acid and water, then dried and concentrated. Chromatography of the residue on silica gel with 1:1 acetone-ethyl acetate gave the product which crystallized from diethyl ether to afford 219 mg, m.p. 151°–153° C.

EXAMPLE 5

17β-N-(2-hydroxyethyl)carbamoyl-4-methyl-4-aza-5α-androstan-3-one

By replacing the 2-methyl-2-aminopropanol of Example 4 with ethanolamine there was obtained a product of m.p. 119°–121° C.

EXAMPLE 6

17β-N-(carbomethoxymethyl)carbamoyl-4-methyl-4-aza-5α-androstan-3-one

Following the procedure of Example 1 but substituting 4-methyl-3-oxo-4-aza-5α-androstane-17β-carboxylic acid for the acid and methylglycinate for the amino compound there was obtained a product of m.p. 217°–219° C.

EXAMPLE 7

17β-(N-carboxymethylcarbamoyl)-4-methyl-4-aza-5α-androstan-3-one

A solution of 450 mg of the product of Example 6 with 250 mg of potassium carbonate, 1.2 ml of water and 12 ml of methanol was refluxed for 16 hours. The mixture was concentrated under reduced pressure and the residue was washed with chloroform. The residue was dissolved in water and acidified with hydrochloric acid. The separated solid was washed with water and dried to leave 432 mg of the product, m.p. 160°–162° C.

EXAMPLE 8

17β-N-(2-hydroxymethyl-2-propyl)carbamoyl-4-aza-5α-androstan-3-one

A mixture of 235 mg of S-(2-pyridyl)-3-oxo-4-aza-5α-androstane-3-17β-thiocarboxylate and 420 mg of 2-amino-2-methyl-1-propanol and 5 ml of tetrahydrofuran is stirred at 25° C. for 24 hours. The insoluble product is separated and washed with tetrahydrofuran and ether to leave 173 mg, identified by its NMR spectrum.

EXAMPLES 9 and 10

17β-N-(2-carboxy-2-propyl)carbamoyl-4-aza-5α-androstan-3-one and
17β-N-(2-carbomethoxy-2-propyl)carbamoyl-4-aza-5α-androstan-3-one Using the procedures of Examples 2 and 3, the product of Example 7 is converted successively into the title compounds of these Examples, identified by their mass and NMR spectra.

What is claimed is:

1. A compound of the formula:

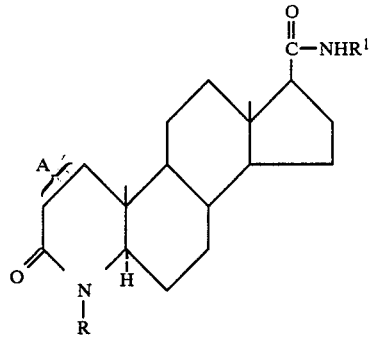

wherein
R is hydrogen, methyl or ethyl;
$R^1$ is $C_{1-12}$ straight or branched chain alkyl wherein one of the hydrogens is substituted by hydroxy, carboxylic acid or $C_{1-4}$ alkyl ester; and
A is —$CH_2$—$CH_2$— or —CH═CH—,
or the pharmaceutically acceptable salts thereof.

2. A compound of claim 1 of the formula:

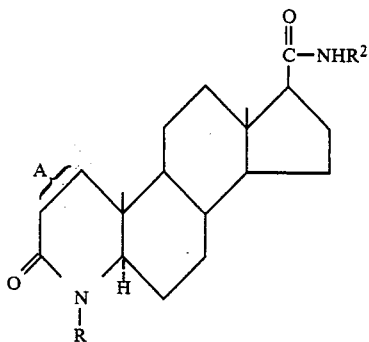

wherein

R is hydrogen, methyl or ethyl; and $R^2$ is $C_{3-8}$ branched chain alkyl wherein one of the hydrogens is substituted by hydroxy, carboxylic acid or $C_{1-4}$ alkyl ester; and A is —$CH_2$—$CH_2$ or —CH=CH—.

3. A compound of claim 2 wherein R is hydrogen or methyl, $R^2$ is $C_{3-8}$ branched chain alkyl having one of the hydrogens substituted by hydroxy, carboxylic acid or $C_{1-4}$ alkyl ester, and A is —C≡C—.

4. A compound of claim 1 which is

17β-N-(2-hydroxymethyl-2-propyl)carbamoyl-4-aza-5α-androst-1-en-3-one;

17β-N-(2-carboxy-2-propyl)carbamoyl-4-aza-5α-androst-1-en-3-one;

17β-N-(2-carbomethoxy-2-propyl)carbamoyl-4-aza-5α-androst-1-en-3-one.

5. A compound of claim 4 in substantially pure form.

6. A compound of claim 1 which is:

17β-N-(2-hydroxyethyl)carbamoyl-4-methyl-4-aza-5α-androstan-3-one;

17β-N-(carbomethoxymethyl)carbamoyl-4-methyl-4-aza5α-androstan-3-one;

17β-(N-carboxymethylcarbamoyl)-4-methyl-4-aza-5α-androstan-3-one;

17β-N-(2-hydroxymethyl-2-propyl)carbamoyl-4-aza-5α-androstan-3-one;

17β-N-(2-carboxy-2-propyl)carbamoyl-4-aza-5α-androstan-3-one;

17β-N-(2-carbomethoxy-2-propyl)carbamoyl-4-aza-5α-androstan-3-one.

7. A method of treating the hyperandrogenic condition of acne vulgaris, seborrhea, female hirsutism, and benign prostatic hypertrophy which comprises administering to a patient in need of such treatment a therapeutically effective amount of a compound of claim 1.

8. A method of inhibiting testosterone 5α-reductase in a patient in need of such inhibiting treatment, which comprises administering to such a patient of a therapeutically effective amount of a compound of claim 1.

9. A pharmaceutical composition comprising a pharmaceutically acceptable carrier and an anti-hyperandrogenic condition effective amount of a compound of claim 1.

* * * * *